US008784350B2

(12) United States Patent
Cohen (10) Patent No.: US 8,784,350 B2
(45) Date of Patent: Jul. 22, 2014

(54) AUTO-ACCOMMODATING THERAPEUTIC BRACE

(76) Inventor: Donald M. Cohen, Irvine, CA (US)

( * ) Notice: Subject to any disclaimer, the term of this patent is extended or adjusted under 35 U.S.C. 154(b) by 143 days.

(21) Appl. No.: 12/964,608

(22) Filed: Dec. 9, 2010

(65) Prior Publication Data
US 2012/0150086 A1  Jun. 14, 2012

(51) Int. Cl.
*A61F 5/00*  (2006.01)
(52) U.S. Cl.
USPC ..................... 602/27; 128/DIG. 20
(58) Field of Classification Search
USPC ............. 602/5, 16, 20, 21, 23, 26, 27, 13; 128/882, DIG. 20; 601/5, 33, 34, 35, 601/148–151; 606/201, 202
See application file for complete search history.

(56) References Cited

U.S. PATENT DOCUMENTS

| | | | |
|---|---|---|---|
| 2,467,907 A | 4/1949 | Peckham | |
| 4,551,933 A * | 11/1985 | Morell et al. | 36/118.9 |
| 4,565,017 A * | 1/1986 | Ottieri | 36/117.8 |
| 4,596,080 A * | 6/1986 | Benoit et al. | 36/118.9 |
| 4,637,382 A | 1/1987 | Walker | |
| 4,662,087 A | 5/1987 | Beuch | |
| 4,669,202 A * | 6/1987 | Ottieri | 36/118.5 |
| 4,711,242 A | 12/1987 | Petrofsky | |
| 4,730,403 A | 3/1988 | Walkhoff | |
| 4,850,877 A | 7/1989 | Mason et al. | |
| 4,977,691 A * | 12/1990 | Orchard, 3rd | 36/44 |
| 4,995,173 A | 2/1991 | Spier | |
| 5,113,599 A | 5/1992 | Cohen et al. | |
| 5,125,400 A | 6/1992 | Johnson, Jr. | |
| 5,259,832 A | 11/1993 | Townsend et al. | |
| 5,277,698 A | 1/1994 | Taylor | |
| 5,330,418 A | 7/1994 | Townsend et al. | |
| 5,472,412 A | 12/1995 | Knoth | |
| 5,490,831 A | 2/1996 | Myers et al. | |
| 5,827,209 A * | 10/1998 | Gross | 602/19 |
| 5,899,869 A | 5/1999 | Barrack, Jr. et al. | |
| 5,931,796 A | 8/1999 | Kellenberger | |
| 5,934,599 A | 8/1999 | Hammerslag | |
| 6,024,713 A * | 2/2000 | Barney | 602/23 |
| 6,202,953 B1 | 3/2001 | Hammerslag | |
| RE37,297 E | 7/2001 | Smith, III | |
| 6,289,558 B1 | 9/2001 | Hammerslag | |
| 6,319,215 B1 * | 11/2001 | Manor et al. | 601/152 |
| 6,635,024 B2 | 10/2003 | Hatton et al. | |
| 6,685,661 B2 * | 2/2004 | Peled | 601/149 |
| 7,163,518 B1 * | 1/2007 | Roche et al. | 602/11 |
| 7,311,687 B2 | 12/2007 | Hoffmeier et al. | |
| 7,507,215 B2 * | 3/2009 | Ryan | 602/23 |
| 7,918,811 B2 * | 4/2011 | Lussier et al. | 602/23 |
| 7,993,292 B2 * | 8/2011 | Sterling et al. | 602/13 |
| 8,046,937 B2 * | 11/2011 | Beers et al. | 36/50.1 |
| 8,083,704 B2 * | 12/2011 | Jensen et al. | 602/23 |

(Continued)

*Primary Examiner* — Patricia Bianco
*Assistant Examiner* — Raymond E Harris
(74) *Attorney, Agent, or Firm* — Fish & Tsang LLP (57) ABSTRACT

The current invention is an accommodating apparel or brace. It is intended to be convenient and comfortable. When the brace wearer is at rest, the brace exerts only modest forces against the body. When the brace wearer is active, the brace tightens and diverts load to protect the body part. The brace accommodation may include application of stronger fixation when activity begins and which persists as long as the activity does. It may also include application of forces around the body part to shift load away from the target part. The accommodation also includes relaxation of forces applied to the wearer when the wearer relaxes.

7 Claims, 8 Drawing Sheets

(56) References Cited

U.S. PATENT DOCUMENTS

| | | |
|---|---|---|
| 8,202,239 B2 * | 6/2012 | Wilkerson ............... 602/27 |
| 8,262,595 B2 * | 9/2012 | Guldalian ............... 602/13 |
| 2001/0018564 A1 * | 8/2001 | Manor et al. ............ 601/152 |
| 2005/0240135 A1 | 10/2005 | Hoffmeier et al. |
| 2006/0135902 A1 | 6/2006 | Ingimundarson et al. |
| 2007/0010772 A1 | 1/2007 | Ryan |
| 2007/0232977 A1 | 10/2007 | Castillo et al. |
| 2007/0249977 A1 * | 10/2007 | Bonnefin et al. ......... 602/13 |
| 2009/0198163 A1 * | 8/2009 | Senyei et al. ........... 602/18 |
| 2009/0272007 A1 | 11/2009 | Beers et al. |

* cited by examiner

AUTO-ACCOMMODATING THERAPEUTIC BRACE

FIELD OF THE INVENTION

The field of the invention is supportive apparel, such as orthopedic or therapeutic braces. More specifically the field is accommodating braces that change in response to activity, or physiological and therapeutic needs of the wearers. Principal applications are reduction of force borne by arthritic joints or compromised body parts (as with foot ulcers) and semi-automatic apparel (such as shoes).

BACKGROUND

Supportive apparel is needed and used by many people. For example, many people employ orthopedic or therapeutic braces to reduce loading to a particular portion of the body. Supportive apparel also includes footwear.

Orthopedic/Therapeutic Braces

There are many people who have clinical need to reduce the force borne by a particular surface—such as the surface of an arthritic joint, or the plantar foot surface when there is a foot ulcer.

Many people experience joint pain. In fact, it is estimated that well over 20 million Americans suffer from the effects of osteoarthritis—a condition in which there is breakdown or erosion of the cartilage that lubricates the bearing surfaces of the bones in a joint. This results in pain and stiffness.

Cartilage protects bone surfaces at joints and produces fluid to lubricate the joint. When too much cartilage in a joint is worn away, compression in the joint can push two unlubricated bone surfaces together. When the joint is flexed and the unlubricated surfaces are moved against each other, the pain can be severe.

The pain of osteoarthritis is exacerbated when the unprotected bone surfaces are pushed against each other—as for example pain from an arthritic knee during walking. Without load bearing, the osteoarthritis patient may well have full range of motion in the joint, but the pain of bearing weight pushes bone against bone (without the protective effect of cartilage and synovial fluid) and thus makes even walking unbearably painful. If the bone surfaces could be kept apart even a minute distance, then the pain would subside.

Treatments utilized by these patients include anti-inflammatory medication, analgesic medication, extracorporeal prosthetic (cane or brace), implanted prosthetic (joint replacement) or injection of lubricious media.

Braces are of several varieties. One variety limits range of motion, mostly to limit potentially harmful movement in patients following injury or surgery. Another variety of brace is an unloader brace—which is intended to provide relief mostly for those with arthritis. When an unloader brace is functioning in accordance with the design principles, eccentric forces are applied to avoid the most damaged portion of the joint. Compressive force on the cartilage deficient bone portion of the joint is reduced. This brace often accomplishes its goal by shifting the load medially or laterally away from the most damaged portion of the joint. Alternatively it is simply applied tightly enough as to cause an increase in the gap between bone surfaces—as by reverse barreling or the Poisson effect. There are many unloading knee brace products and patents, for example U.S. Pat. No. 5,277,698.

Other braces are also intended to be affixed to the person and bear all or part of the load of the affected joint; and in addition have a mechanism to lock the brace. For example U.S. Pat. No. 5,490,831 discloses a knee brace in which the articulating hinge can be locked at a fixed angle to assist in walking. The brace incorporates a heel strike mechanism as a trigger for the locking mechanism. Similarly, U.S. Pat. No. 6,635,024 discloses a brace that can be manually locked to allow the brace to support the weight of the patient while standing.

Foot Ulcers

Another big need for an accommodating brace is reduction of load borne by foot ulcers during normal walking activity. Load on foot ulcers inhibits healing and exacerbates the condition. If the ulcers are not healed, amputation can be necessary to preserve the life of the patient.

There are about 20 million diabetics in the US and about 200 million worldwide. 15% of diabetics develop foot ulcers during their lifetimes. Every year about 5% of diabetics develop foot ulcers. There are about 120,000 hospital amputations of lower extremities each year in the US, 60% of these are diabetic patients. It has been reported that it typically costs over $20,000 to treat a foot ulcer over the 2 years following the initial diagnosis. Clearly there are good reasons, financial and compassionate to reduce the severity of foot ulcers, and to promote healing. This can be accomplished by the use of a brace that reduces or eliminates the load on the foot during normal activities.

A frequent complication to foot ulcers is neuropathy that severely reduces patients' ability to sense foot pressure or pain. Without this feedback, patients will be unaware of continued damage due to unsafe loading of the affected area. Consequently, more passive treatment approaches are necessary to treat these patients.

Treatment of foot ulcers includes dressing and debridement, braces, orthotics, footwear and even total contact casting (in which the foot and lower leg are encased in a cast to inhibit weight bearing on the foot ulcer). It is crucial to reduce load bearing of foot ulcers, because load bearing retards or even reverses the healing process.

Foot Apparel

Another closely related technology is closure and tightening technologies for athletic footwear. In 1989 Reebok sold athletic shoes that used a manually operated integral air pump to tighten the fit of shoes. Competitors for the Reebok Pump included LA Gear Regulators and Nike Air Pressure. There are many patents that disclose inventions that use bladders and other systems to allow the user to manually improve fit, beyond the conventional lacing or Velcro strap systems, such as U.S. Pat. No. 4,662,087, U.S. Pat. No. 4,763,426, U.S. Pat. No. 5,113,599 and U.S. Pat. No. 4,995,173.

Another patented athletic shoe closure includes the Boa system, and the U.S. Pat. Nos. 5,934,599, 6,202,953, 6,289,558. These shoes use a manually operated reel to snug a cable that tightens the fit of the shoe.

Patent application 20090272007 Automatic Lacing System of Beers et. al. assigned to Nike, Inc. teaches a lacing system for footwear that uses a motor to drive an assembly that tightens laces or straps when activated. This is reputed to be the power laces system that gained notoriety when depicted in the film Back to the Future II.

Limitations of Present Technologies

The aforementioned treatment alternatives have limitations. The medication treatment options can reduce pain, infection and inflammation in many people—though often incompletely. Additionally, these can have deleterious systemic side effects. These unwanted effects can sometimes be severe—such as ulceration and hemorrhage (particularly gastro-intestinal).

Use of a cane to relieve the pain of an arthritic knee indeed has some history of success by diverting weight to the arm instead of the knee. The knee thus does not have to bear as much compression so the compressive and shear stresses experienced by the surfaces of the femur and tibia are diminished. Understandably, the lower stresses result in diminution of pain. Of course the use of a cane mandates an unnatural gait and occupies one hand—so a cane does have large limitations. Additionally, the off-loading by a cane is highly variable and unreliable, especially with patients who have neuropathy.

Implanted total or partial joint replacement can greatly relieve symptoms. Limitations of this solution include cost, pain and risk of surgery. Also, any failure of the replacement joint necessitates additional surgery and attending cost, pain and risk.

Injection of lubricious media (such as viscous hyaluronic acid) within a joint has experienced mixed results. There has been relief of arthritis symptoms—though generally temporary.

Often arthritis sufferers have asymmetric joint wear. A person who has excessive cartilage wear in the medial portion of the joint may benefit from an unloader brace that shifts the load laterally. This is generally accomplished by judicious application of the attachment straps that redistribute the weight of the patient through the less diseased portion of the joint. This implies that the healthier portion of the joint bears a larger than normal load. For an unloader brace to function properly, it must be tight—tight enough to force the wearer to stride in an unnatural gait that shifts the load. Thus limitations of the unloader brace are that it can not always achieve sufficient relief of symptoms and that if it is tight enough to do so, that it is often uncomfortable. Additionally, if there is slippage of the brace with respect to the joint the functionality can be compromised.

Braces of the sort disclosed in U.S. Pat. No. 5,490,831 would suffer from similar shortcomings. They must be tight to work at all—slippage frustrates the effectiveness of the braces. In addition they are large and cumbersome. Also, though relatively rigid, they do not reduce the load on the knee as an unloading brace does.

Prior art devices, even those that share load with the joint, are designed to (at most) limit how much the joint is compressed. They can bear part of the compressive load that would otherwise be fully borne by the joint. They do not apply counter force or impose motion in the opposite direction of the compression to spare the joint.

In the treatment of foot ulcers, dressings and debridement can promote healing, but this is futile if the patient continues to apply pressure to the ulcer by walking on it. Braces, orthotics and footwear can reduce the stress on the ulcers, but patients often do not comply with the directive to avoid walking without them. Patients do about 50% of their walking at home, but they only wear the footwear that protects the ulcers about 15% of the time at home. This is because the footwear can be uncomfortable and inconvenient. For this reason, total contact casting is often used, so that the patient cannot remove the footwear. Though this does improve compliance, a cast is heavy and uncomfortable, and it blocks access to the ulcer—compromising the care of the ulcer. Additionally, some suggest that because casting requires more intensive and fairly uncommon "fitting" skills, it is underutilized.

There is thus a need for footwear that is more convenient with better therapeutic potential than currently available options that reduces load on foot ulcers.

It is an objective of the invention to accommodate to user status. It is an objective of the invention to appropriately increase fixation force as needed when the wearer uses the affected joint or body part.

With respect to joint problems, it is an objective of the present invention to provide accommodating apparatus that reduces load on a joint or surface during use.

It is another objective of the invention to apply counter force (or to increase the distance between bearing surfaces of bones in an affected joint) when the brace wearer uses the affected joint. It is a further objective of the current invention to apply unloading force around the joint during load bearing and to substantially remove the unloading force during non-load bearing intervals.

It is a further objective to minimize the degree of slippage of the brace compared to current braces or to automatically reverse the slippage and so to maintain functionality during prolonged used.

Another objective is to continuously and automatically adjust the brace to physiological changes experienced by the patient (e.g. reduced edema) to maintain the targeted off-loading force throughout its prescribed use.

With respect to athletic footwear, the current tightening systems require manual user interface to achieve the optimal fit. There is thus a need for athletic footwear fit systems that require less activity from the wearer; i.e. the shoe should perform more of the work in tightening and or sensing.

Another objective of the current invention is to also apply force on the body to reduce edema, to improve venous drainage and/or to improve arterial perfusion and lymphatic circulation.

ADDITIONAL PRIOR ART INFORMATION

US Patents

U.S. Pat. No. 6,635,024 Articulating knee supports
U.S. Pat. No. 5,490,831 Selectively lockable knee brace
U.S. Pat. No. 5,899,869 Orthopedic appliance with weight activated brake and variable extension assist
U.S. Pat. No. 6,024,713 Leg support apparatus
U.S. Pat. No. 5,277,698 Knee bracing method
U.S. Pat. No. 7,311,687 Osteoarthritis brace
U.S. Pat. No. 2,467,907 Corrective and protective knee brace
U.S. Pat. No. 5,125,400 Ankle brace having multiple inflatable aircells
U.S. Pat. No. 5,931,796 Lower extremity support apparatus
U.S. Pat. No. 5,330,418 Multiaxis controlled motion knee brace with a four bar joint and method for producing same
U.S. Pat. No. 5,259,832 Multiaxis controlled motion knee brace with a four bar joint and method for producing same
U.S. Pat. No. 4,850,877 Method of determining stress effects in components of the human knee and anthropomorphic leg device therefor
U.S. Pat. No. 4,711,242 Control system for knee joint
U.S. Pat. No. 4,637,382 Motion-guiding load-bearing external linkage for the knee
U.S. Pat. No. 5,472,412 Limb brace with adjustable hydraulic resistance unit
U.S. Pat. No. 7,163,518 Walking leg support
RE37297 Dynamic orthopedic knee brace assembly
U.S. Pat. No. 5,934,599 Footwear lacing system
U.S. Pat. No. 6,202,953 Footwear lacing system
U.S. Pat. No. 6,289,558 Footwear lacing system
U.S. Pat. No. 4,662,087 Hydraulic fit system for footwear
U.S. Pat. No. 4,730,403 Pressurized ski boot
U.S. Pat. No. 5,113,599 Athletic shoe having inflatable bladder
U.S. Pat. No. 4,995,173 High tech footwear US Patent Applications 20070232977 Flexible tether member connecting a knee brace to a boot
20060135902 Knee brace and method for securing the same
20070010772 ORTHOTIC BRACE
20050240135 Osteoarthritis brace
20090272007 Automatic Lacing System

SUMMARY OF THE INVENTION

The current invention is automatic, accommodating apparel. It is intended to be convenient, comfortable, and therapeutically reliable. The apparel may take the form of a foot brace, a knee brace, a back support or other accommodating apparel. As a brace, it partially or completely diverts load off of a body part such as an arthritic knee joint or an ulcerated foot. When the target body part begins to bear load, the brace accommodates, and diverts a portion of the load through the brace, away from the specified or protected body part. When the specified body part ceases activity, the brace accommodates again, and ideally assumes a more comfortable fit for the patient.

The brace partially diverts load off of a body part (such as an arthritic knee joint or an ulcerated foot) when needed. When the target body part begins to bear load, the brace accommodates, and diverts a portion of the load through the brace, away from the target part. When the target body part ceases activity, the brace accommodates again, and ideally becomes more comfortable for the patient.

The apparel apparatus attaches to the body near or around a foot, ankle, wrist, knee, elbow or other body part that requires a reduction in ordinary load for therapeutic application or protection. In general, contemplated apparatus include (1) a fixation apparatus to affixes the apparel to the body proximate the body part, (2) a detection apparatus to detect changes or activity to or of the body, and (3) a mechanism that responds to the detected change to divert load from the body part.

The accommodating action of the apparel may include application of stronger or enhanced fixation when activity begins, i.e. it holds more tightly to the body. It may also include application of forces around the body part to divert load away from the compromised body part. The accommodation preferably also includes relaxation of the forces applied to the wearer when the specified body part no longer needs protection.

As foot apparel for example, it senses the need for a change in fixation; tightening when the user is walking, loosening or unfastening when the user is seated or at rest.

DETAILED DESCRIPTION OF THE INVENTION

The apparel is used to accommodate to the needs of a wearer. It is intended to be comfortable while the wearer is at rest; comfortable enough that the wearer is not prompted to remove the apparel while at rest—as is so common with other load diverting braces.

Apparel is meant to include at least orthopedic brace, sleeve, footwear, glove and belt.

Foot Brace

The accommodating brace may be used to divert load from the foot to the leg of a wearer, as would be appropriate for a patient with a diabetic foot ulcer or for a patient with a foot or ankle injury. A brace to reduce load on foot ulcers would share many characteristics of a brace to reduce load on the ankle. The braces depicted in FIGS. 1 through 5 demonstrate some embodiments of accommodating braces of this sort. During load bearing, the brace tightens to the lower leg, and preferably deflates an in-sole so that some of the load is transferred through the structure of the boot/brace (from the ground to the leg), bypassing the foot and ankle. Fixation can be accomplished by hydraulic or pneumatic bladders, or by straps, or by other equivalent means.

The application of extra fixation pressure can be applied through bladders, straps, cable system (such as the Boa) or other equivalent.

Preferred Embodiment of a Foot Brace

Figure 1A:
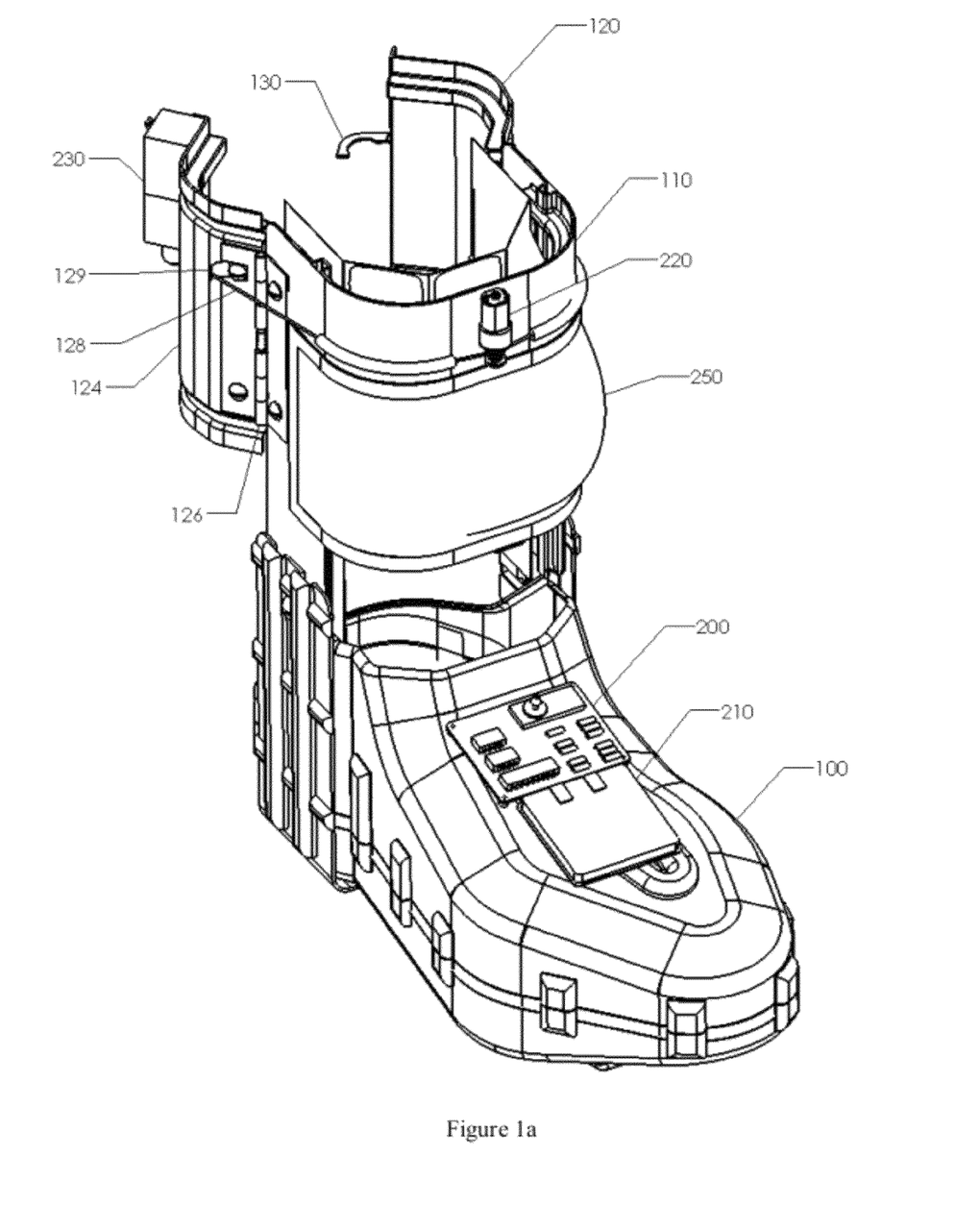
FIG. 1a is an isometric view of the front of the preferred embodiment of most of the interior of an accommodating boot/brace that transfers load that would otherwise be borne by the plantar surface of a foot to the leg. The outer skin of the boot has been omitted to permit view of the molded plastic weight bearing hinged ankle chassis with rear entry doors, battery powered microprocessor controller, door motor and mechanism, door latch and bladder ballast.
Figure 1B:
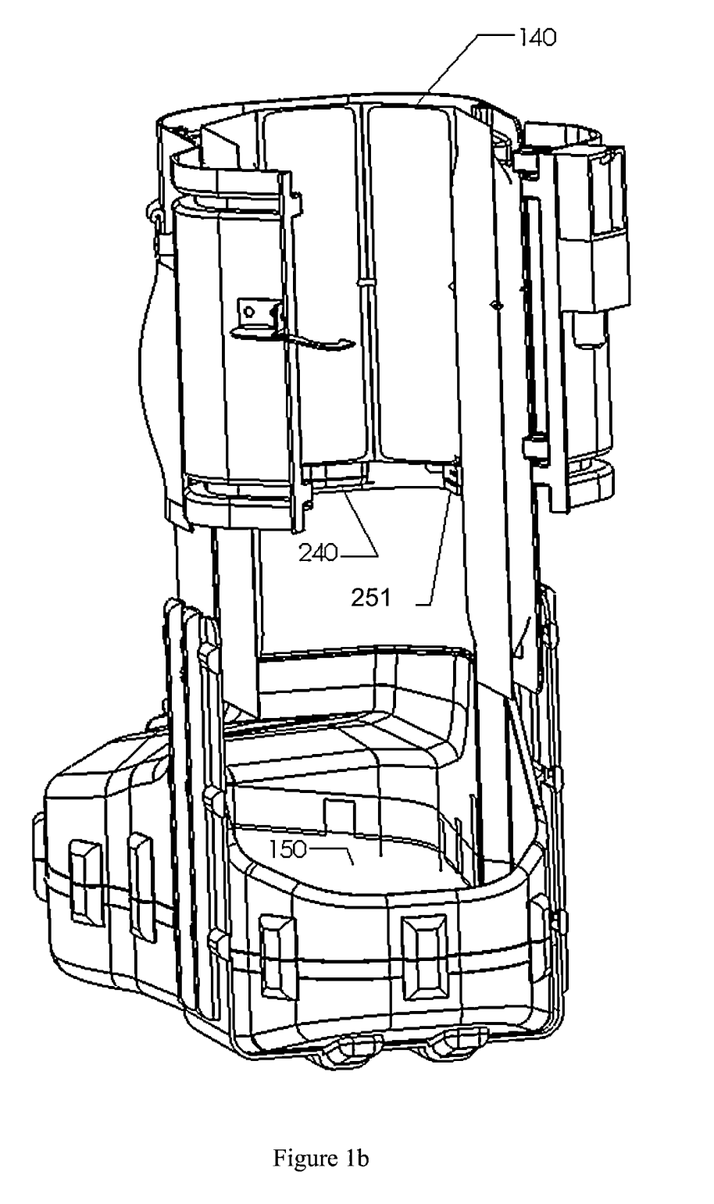
FIG. 1b is an isometric view of the rear of the boot/brace of FIG. 1a. This affords a better view of the compartmentalized leg bladder, the pump and control valves, and the insole bladder.

A description of the preferred embodiment of a brace to be used to aid in the healing of diabetic foot ulcers follows and is depicted in FIGS. 1a and 1b.

The brace or boot is intended to be as easy to put on as a bedroom slipper, yet effective at diverting a portion of the weight of the wearer from the plantar surface of the foot to the lower leg. The chassis of the boot is a subassembly mostly of molded plastic such as PETG. It preferably includes a live ankle hinge with travel stops in both directions and it is strong and rigid enough to bear more than the full weight of the wearer. The chassis may be injection molded, vacuum formed or other equivalent. It is light weight and strong. The chassis consists of a rigid molded shoe 100 that is attached to a rigid molded upper chassis 110 by a hinge joint on each lateral side. The rigid molded left and right rear doors 120 and 124 are attached to the upper chassis by spring loaded hinges (126 on the right side).

Sensing and controlling functions are processed and controlled by the processor/controller mounted on the circuit board 200 and powered by the rechargeable battery 210.

When the wearer dons the boot and the presence of the foot and leg is sensed, the processor signals the gear motor 220 to apply tension to the cable 128 to pull the leaf spring door tab (129 on the right side) to close both doors. When the doors close, they are held securely by the plunger from the latch solenoid 230 and the latch clasp 130.

When the wearer stands or walks, the activity is sensed, and the processor sends signals that tighten the fixation to the leg thus redirecting some load from the bottom of the boot/brace to the leg, thus bypassing the foot. The processor sends a signal to the bladder fill solenoid valve to allow air to transfer from the constant pressure ballast 250 to the compartmentalized leg bladder 140. Once the leg is securely held by the inflated leg bladder, deflation of the insole 150 permits further unloading of the plantar surface.

The deflation of the insole is passive, i.e. weight borne by the insole causes it to deflate slowly. The air is forced out through a restrictive opening so that it would take on the order of a minute to empty, whereas the leg fixation bladders fill on the order of a second. The leg is thus quickly held by the boot, and then the load is reduced from the insole. Load is further diverted away from sites of ulcers, lesions and stress concentrations by the shape of the insole, i.e. low spots or cut-outs.

The volume in the ballast is replenished later as the processor sends signals to the pump 240.

When the wearer ceases standing and walking, the relaxation is sensed, and the processor sends signals to the bladder vent solenoid valve 251 to reduce the fixation force on the leg of the wearer, thus allowing for more comfort, i.e. when the processor confirms the detection of the relaxation state of the wearer, the tightening of the fixation is reversed. With the body weight load removed from the insole, the insole re-inflates passively. The driving force is provided by a foam rubber insert within the insole bladder. Air slowly returns to the insole bladder through the restrictive opening.

A similar alternative for the air bladder insole is a viscoelastic insole in which the height of the insole also reduces slowly with time under load. The insole could alternatively be actively inflated and deflated so that the control of the unloading is more directly influenced by the processor.

When the patient opts to remove the boot, the processor sends signals to the bladder vent solenoid valve and to the solenoid latch to release the latch, and then to the motor to open the doors. The wearer may manually release the latch and open the doors.

The boot allows for rear entry so that a patient can don the boot while seated or standing. The boot includes spring loaded hinged rear doors that are closed by tensioned cables that are pulled by a mid-line mounted gear motor.

Additional padding may be used for a custom fit and enhanced comfort.

When worn, the chassis is covered with a leather, fabric or equivalent fabric for fashion and protection and temperature moderation.

The rigid sole has a rubber covering for traction and shock absorption. The rubber may also include extra rocker, especially for those with locked or no hinge chassis.

The chassis ankle hinge is free to pivot up to a forward and rear lock orientation. The lock assists in transferring load between the upper and lower chassis. In an alternative embodiment the ankle hinge can be locked or even eliminated from the design entirely.

Sensing of the foot and leg in the boot is accomplished by a simple spring switch that is made when the shin closes it by entering the boot fully. This helps to avert premature detection and closing of the doors. There are many acceptable equivalent alternatives, such as a load sensor under the forward portion of the insole or optical sensor. Sensing of standing and ambulation may be accomplished with the load sensor, with an accelerometer on the processor board or equivalent.

The door latch may be a solenoid latch, a motor driven latch, pneumatic closure or equivalent.

The medium to pressurize the ballast and the bladder is air, but may be water, hydraulic fluid or other equivalent. A big advantage of air is the lightweight assembly and the omnipresence of air supply.

The leg bladder is divided into compartments for improved fit, but fills as one. Compartments that fill separately are acceptable, and in fact allow for a more customized fit and sequential pressurization. The bladder walls are preferably heat sealed high density polyethylene film, pvc film or other equivalent.

The ballast allows for rapid filling of the bladder; at a rate faster than the miniature pump can provide. The ballast is designed to provide a large volume of air at a nearly constant pressure in the range of 1 to 5 psi. The constant pressure ballast may use a pressure regulated output, may be constructed of a super-elastic body or membrane, may use constant force extensor springs or may use other equivalent to deliver a nearly constant pressure output. Preferably the ballast uses a latex membrane for its high elongation and flat elastic modulus behavior. The ballast may be eliminated entirely; and the pump may fill the bladder directly.

The valves may be 2 way or 3 way, may be discrete or manifold ganged or other equivalent. They may be solenoid, piezoelectric or other equivalent.

Figure 6:
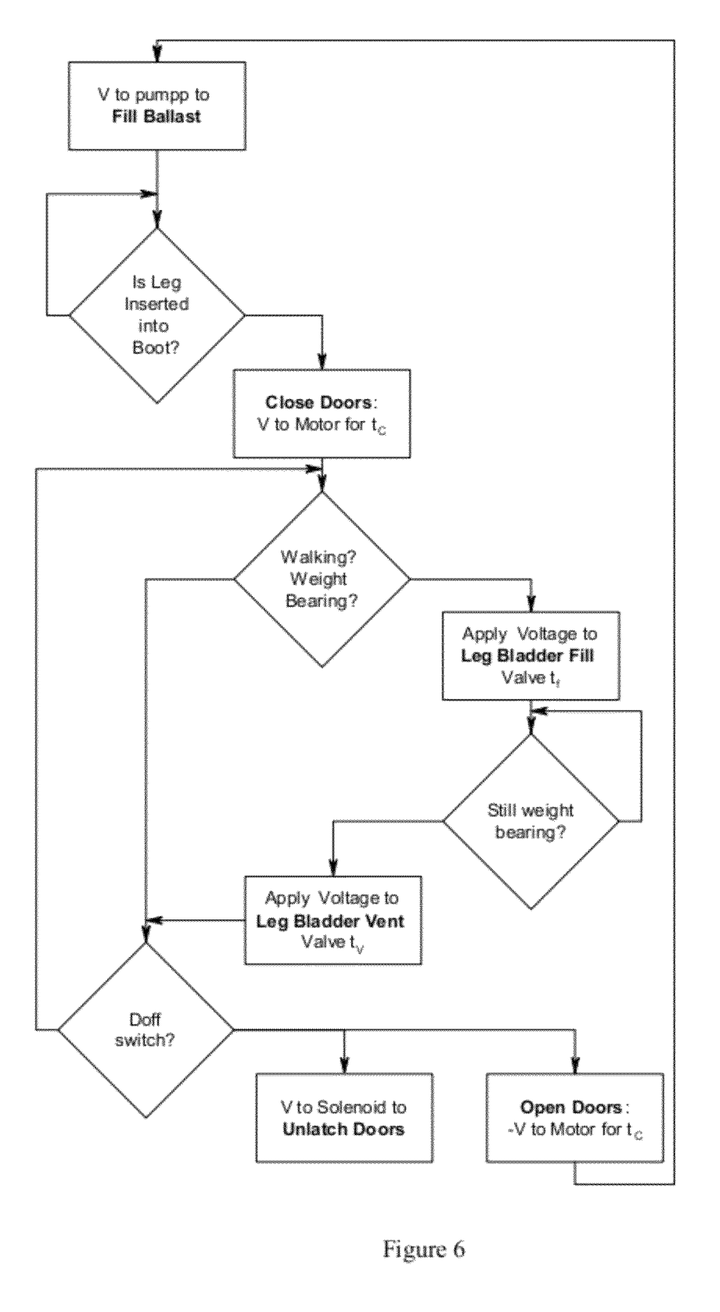
FIG. 6 is a top level flow chart for a preferred embodiment of a diabetic foot ulcer boot.

Connections among the components are made using flexible pvc or silicone tubing or equivalent A top level flow diagram for the process is shown in FIG. 6. Beginning at the top, the processor operates the pump to assure that the ballast is filled with pressurized air. It remains at the ready until a sensor indicates that the leg is fully inserted into the boot, whereupon it sends signals to the motor to close the doors. The boot may remain in this state indefinitely. When weight bearing activity is detected, the processor applies signals to the bladder fill valve to allow pressure to the bladder to affix tightly to the leg. This allows the wearer to walk with full brace support. The insole plantar bladder passively deflates to allow further unloading. The processor continually rechecks to confirm that the wearer is still weight bearing, i.e. standing, walking, ambulating. When a sensor indicates that weight bearing has ceased, the leg bladder fixation pressure is eased for the comfort of the patient. At this point the boot remains idle as the processor continually checks to see if the patient resumes weight bearing or elects to doff the boot. If weight bearing is resumed, the processor repeats the actions that unload the foot. If on the other hand, the patient has manually elected doffing, the processor releases and opens the doors. It then sends signals to refill the ballast and await the next insertion of the leg into the boot.

As used herein, the terms attach and affix refer to coupling of the apparatus to the body in the manner of a removable brace, i.e., by compression and friction.

Enhancements may be incorporated into the process. For example, all of the processes may be closed loop, rather than the open loop timed events of the preferred embodiment. Sensors can be incorporated to indicate when the ballast is full, when the doors are closed or fully open and when the bladder is at pressure. Sensors can also detect boot fixation slippage, and can detect level of activity. The processor can respond with higher fixation and unloading levels to respond to higher demands. Running is a higher demand than walking; walking is higher than standing.

Sensors can be incorporated which sense and cause response to any of the following: position of the body part or a neighboring body part or brace part, speed of the body part or a neighboring body part or brace part, acceleration of the body part or a neighboring body part or brace part, angle of the body part or a neighboring body part or brace part, height of the body part or a neighboring body part or brace part, presence or absence of a body part in proximity to the apparel, force or stress on the body part or a neighboring body part or brace part, temperature of the body part or a neighboring body part or brace part, change of temperature of the body part or a neighboring body part or brace part, color or change of color of the body part or a neighboring body part or brace part. These apply to a foot brace or boot, a knee brace or other brace or apparel.

The processor thus accepts sensor data and establishes parameter values indicative of the body part at rest or relaxation state. It identifies a range that is indicative of the body part not at rest, i.e. active or load bearing. The processor controls the brace to accommodate to the activity; comfortable while at rest; yet applied fixation and unloading or counter force applied during activity or non-relaxation. The response is preferably binary, but may alternatively be proportional, i.e. the magnitude of the response is proportional to the value of a parameter that is indicative of the level of activity or the amount of support required.

Changes that affect the body part and sensed. When the processor determines that the change is adequate to indicate that the wearer is no longer in a relaxed state, the processor sends a control signal to accommodate or change an aspect of the brace/apparel. The aspect is preferably tightness of the brace, but may be other aspects as well. The aspect of the brace changed may be a dimensional change in the brace, a change in force at an interface between the body and the brace, a change in pressure in a portion of the brace (such as a bladder).

If slippage of the brace is sensed and confirmed by the processor/controller, the processor/controller can send signals that result in repositioning of the brace closer to a preferred position. The repositioning of the brace can be accomplished in an "inch-worm" fashion. In the case of a foot brace, this could involve a momentary partial deflation of a leg fixation bladder then an increase in inflation of an insole bladder during a leg swing phase of gait. This allows the brace to move back towards the preferred position and refasten the fixation in the improved position. Similarly, this can be accomplished by proper sequential operation of thigh fixation bladder, calf fixation bladder and longitudinal extension actuator in a knee brace. This allows the brace to "crawl" up a leg, preferably while unloaded.

The insole plantar bladder is passive, but could also be actively inflated and deflated to permit even finer degree of control, e.g. programmable degree of unloading of the foot.

The boot is available in a variety of sizes to allow close fit to different foot dimensions of different wearers. To allow for an even better fit, there can be custom fitting of the boot to the individual. This entails insertion of pads/spacers between the flesh and the boot. In the preferred embodiment, the custom fit spacer is an extensible container that is filled by a fitting practitioner (such as an orthotist) to allow the bladder to more closely fit the wearer. This allows for a more comfortable fit and also allows for faster accommodation during use since the change in bladder volume (between relaxed state and active state) is optimized. The extensible container spacer is filled with a material that can be poured or injected into the container and then hardens or sets quickly once fit to the wearer. The fill material is injectable polyurethane foam or equivalent. The extensible container may be fabricated from flexible sheets of polyethylene.

Figure 2A:
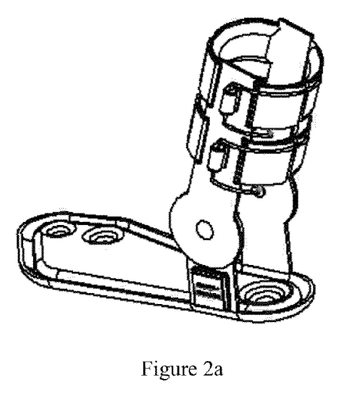
FIG. 2a is an isometric view of a hinged ankle foot brace, affording views of air pumps, inflatable leg straps, inflatable sole, rigid bottom, ankle hinge and processor unit; in this view the straps are fastened but not inflated; the sole is inflated.
Figure 2B:
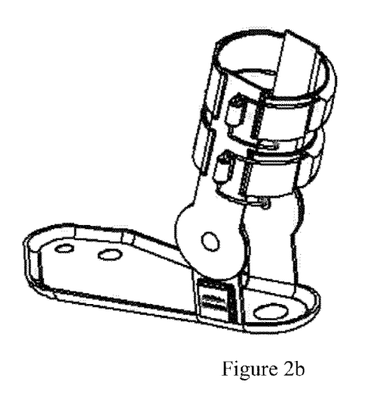
FIG. 2b is an isometric view of the brace of FIG. 2a; in this view the straps are fastened and inflated; the sole is deflated.

Other alternative foot brace embodiments are depicted in FIGS. 2-5. The embodiment of FIG. 2 illustrates how the invention can be incorporated into a device that more closely resembles a conventional ankle brace than a boot. It can be appreciated from the figures that the compared to the bladders in FIG. 2*a*, the leg bladders are inflated in FIG. 2*b*, thus gripping the leg tightly. The plantar bladder of 2*b* is deflated, thus diverting some of the load bearing to the leg. It can be further appreciated that pressure at specific sites is further reduced by the shape of the plantar bladder.

Figure 3A:
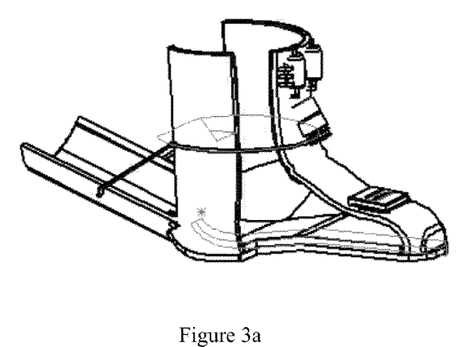
FIG. 3a shows an isometric view of a rear entry hinged back boot with the front right section depicted in cut-away view allow better visualization of the inflatable boot liners and inner sole. Also seen in this view are the cables that lift the hinged back into place, the motor and gear head to pull the cables, a pump to inflate the bladders, a valve manifold to direct the pressure, and a package that includes sensors, battery and processor/controller to detect foot insertion and walking and to control the pump, valves and motor. In this figure, the hinged back of the boot is shown in an open position that allows for easy foot insertion. The bladders surrounding the leg can be seen to be in deflated configuration. The in-sole is seen to be in the inflated configuration.
Figure 3B:
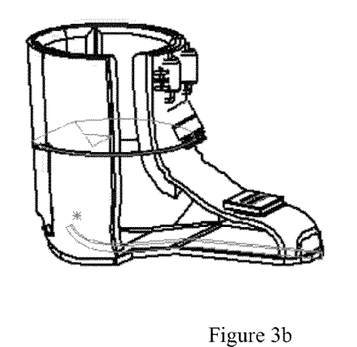
FIG. 3b depicts the boot of FIG. 3a in a configuration where the controller has operated the motor to pull the back of the boot towards the closed position (normally following foot insertion); has operated the motor to pull the back of the boot to the closed position; has operated the pump and valve manifold to inflate the bladders surrounding the leg, as would be consistent with the detection of walking/load bearing; and has operated the valve manifold to deflate the in-sole in order to partially transfer walking load from the bottom of the foot to the leg via the structure of the boot.
Figure 4A:
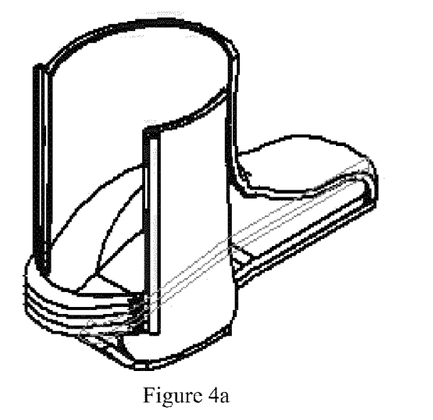
FIG. 4a is an isometric view of an accommodating foot brace boot shown with a partial cut-away of the front right region. This figure affords views of a rigid outer shell, an extendible, inflatable posterior calf support, inflatable anterior leg support and inflatable inner sole. In this view the boot is prepared for easy foot insertion; the posterior leg support is retracted, the anterior and posterior leg supports are deflated and the sole is inflated.
Figure 4B:
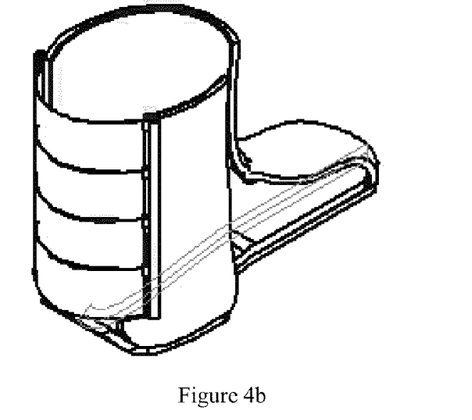
FIG. 4b is the boot of FIG. 4a shown from the same isometric perspective and partial cut-away. In this view the boot is depicted in the configuration corresponding to foot presence in the boot; the posterior leg support is extended, the anterior and posterior leg supports are still deflated and the sole is still inflated.
Figure 4C:
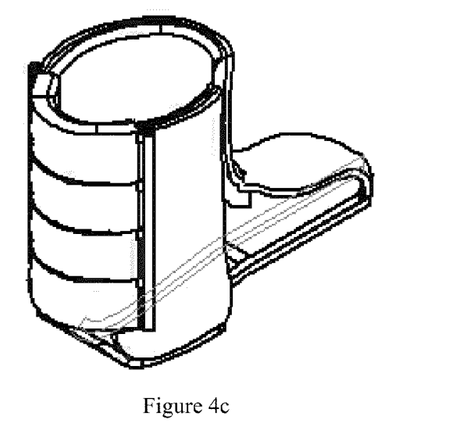
FIG. 4c is the boot of FIGS. 4a and b shown from the same isometric perspective and partial cut-away. In this view the boot is depicted in the configuration corresponding to weight bearing; the posterior leg support is still extended, the anterior and posterior leg supports are now inflated providing fixation force to the leg and the sole is still inflated.
Figure 4D:
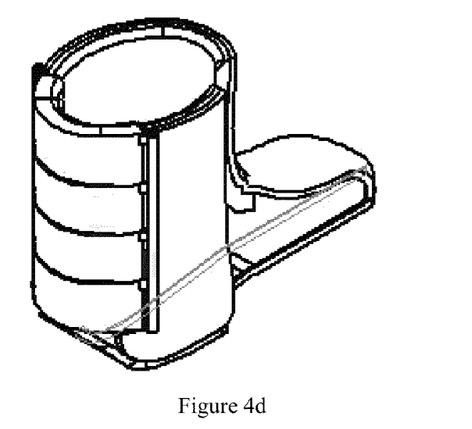
FIG. 4d is the boot of FIGS. 4a, b and c shown from the same isometric perspective and partial cut-away. In this view the boot is depicted in the configuration corresponding to walking; the posterior leg support is still extended, the anterior and posterior leg supports are still inflated and the sole is now deflated, thus reducing load on the sole.

The boot depicted in FIG. 3 resembles a rear entry ski boot, though it adds automaticity to allow for accommodation to the needs of the wearer. It uses a motor driven cable drive to close the door, and uses pneumatic bladders to affix to the leg and to reduce pressure on the plantar surface.

The boot of FIG. 4 is similar to that in FIG. 3 though it utilizes a pneumatic curtain to permit rear entry and leg fixation. This boot requires very little rear side clearance, so it can be donned even when it sits very close to furniture such as the edge of a bed or chair.

Figure 5A:
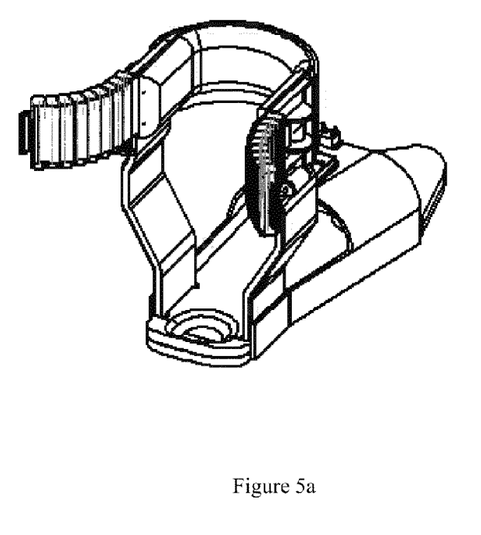
FIG. 5a isometrically depicts the skeleton of a brace awaiting foot insertion.
Figure 5B:
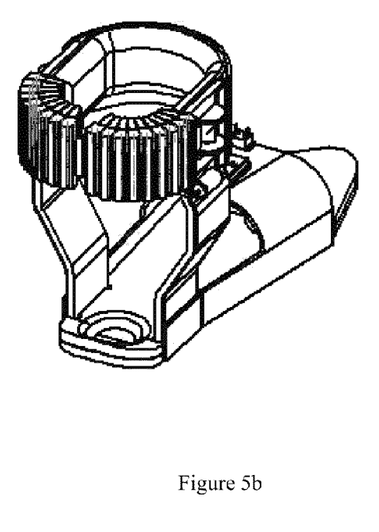
FIG. 5b depicts the structure of the boot in a closed latched inflated position corresponding to weight bearing.

The boot of FIG. 5 depicts a multi-element cable driven rear entry closure mechanism.

Many other configurations are acceptable alternatives, such as top, side or front loading—which may allow for easier donning of the boot, particularly from a seated position.

Automatic Accommodation

Prior art devices have typically required manual accommodation/control. For example, a brace wearer manually dons a brace in anticipation of activity such as walking. The wearer typically bends over and pulls the brace, shoe or boot on while pushing the foot forward. Then the wearer manually fastens or closes and tightens the brace, shoe or boot. In contrast, the preferred embodiment closes around the foot automatically and then latches closed. Further, the preferred embodiment detects when the boot needs to be tightened, and then does so automatically. Further, the preferred embodiment detects when the boot can be safely loosened for comfort, and then does so automatically. The boot closure, the fixation bladder inflation and deflation are all automated.

A person using a typical prior art brace will consciously decide to loosen the fixation of the brace when the person will be idle for a while. In contrast, the preferred embodiment brace will detect automatically the idleness of the person, and in this fully automatic version it will automatically loosen the fixation for comfort.

The boot/brace may be operated in a variety of semi-automatic modes as well. The activation of boot closure and fixation bladder inflation and deflation may each be controlled by the wearer instead of by the processor/controller. Activation of in-sole deflation may also be triggered by the wearer instead of the processor/controller.

In a semi-automatic embodiment of the invention, a sensor on the brace will detect the activity level and alert the wearer of the condition. For example, a sensor can detect that the body part is bearing more load than intended, and so the boot will deliver an alert to the patient to suggest additional tightening of the fixation and reduction in pressure in the in-sole.

In the preferred embodiment, detection of the state of the wearer (at rest or active) triggers the brace to accommodate accordingly.

Knee Brace Embodiment

For those with arthritis, the brace is meant to ease the symptoms of joint pain during load bearing—in which the pain subsides when the load is removed. A primary application is osteoarthritis of the knee. In such a knee, the cartilage that provides the lubrication that allows the knee to flex freely is eroded. The brace applies counter tension to the knee joint at least during load bearing. This tension pulls the femur and tibia apart just enough to allow synovial fluid to infiltrate the area thus reducing the pain of bone on bone flexion and reducing the rate of erosion of the remaining cartilage. The counter tension is removed so that the brace is not uncomfortable after the load bearing ceases.

Figure 7:
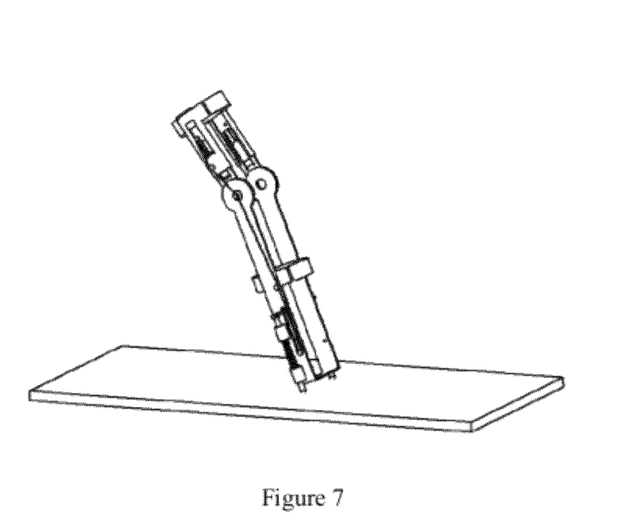
FIG. 7 is an isometric view of a knee brace of the present invention depicted in the position in which the heel would strike the floor—initiating a mechanism in which a flexible cable applies counter tension to the knee joint.
Figure 8:
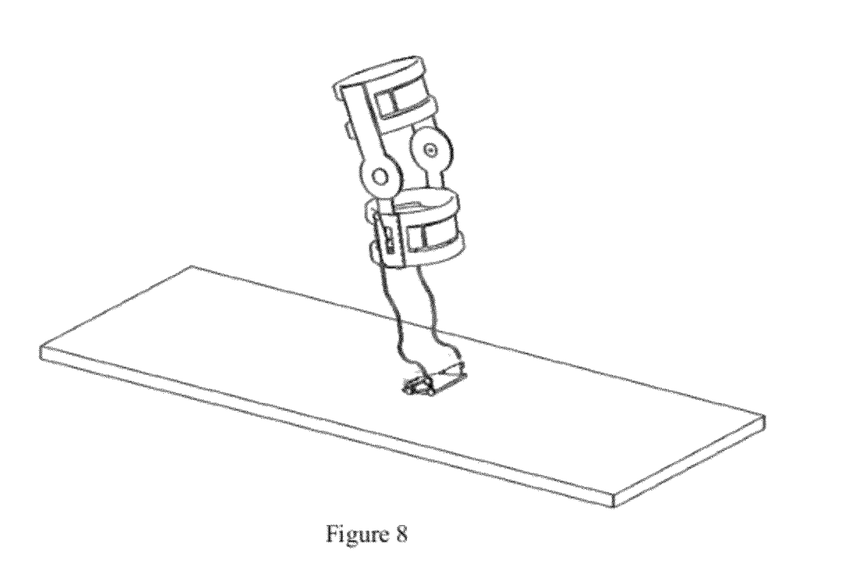
FIG. 8 is an isometric view of another knee brace of the present invention depicted in the position in which the heel would strike the floor—initiating a mechanism in which a flexible cable applies counter tension to the knee joint.

FIGS. 7 and 8 show examples of knee braces in which counter force is applied to the knee with each foot step. A portion of the weight of the body is used to pull the lower leg fixation away from the upper thus reducing load and increasing clearance in the knee joint.

Figure 9:
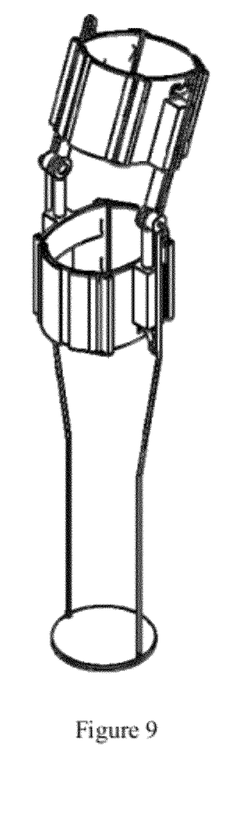
FIG. 9 is an isometric view of a hydraulic knee brace of the present invention in which a hydraulic fluid applies fixation forces to the leg and counter tension to the knee joint whenever load is applied to a hydraulic reservoir positioned under the foot.

In more preferred embodiments the brace is composed of a lower leg collar, an upper leg collar, a pivot, an automatic counter tension mechanism and automatic fixation tighteners as in FIG. 9.

In a preferred embodiment of the current invention, the upper and lower leg collars are similar to those common in the art. The upper and lower leg collars are lightweight, rigid subassemblies that are fastened to the skin of the lower and upper leg respectively using conventional Velcro straps. The straps are tightened enough to hold the brace in place so that its own weight does not displace it. The straps need not be tightened uncomfortably—as would be done with a conventional unloader brace. There is a hinge or pivot connecting the collars and allowing for a full range of motion to permit a normal stride.

The upper leg collar of the brace is attached to the skin on the proximal side of the affected knee. The lower leg collar of the brace is attached to the skin on the distal side of the knee.

While the wearer is at rest, the brace is intended to relax so that it is less uncomfortable to the wearer.

General Version of the Knee Brace

Similar versions of the brace may be use on other joints. In general, this version of the invention consists of a proximal collar to attach to the skin of the wearer on the proximal side of the joint, a distal apparatus (which may attach to the skin on the distal side of the joint or may extend all the way to the ground in an embodiment with lower extremity use), and apparatus to apply force between these two to at least partially counteract a compressive load that would otherwise be borne by the joint. Preferably, the counter force is triggered by the presence of the compressive load on the joint. After the compressive load diminishes, the counter force diminishes as well. Preferably, the counter force is triggered by the compressive load; and the reduction of the counter force is triggered by the reduction in the compressive load. Preferably the tightness of the fixation to the skin is also triggered by the presence of the compressive load. The brace fixation tightness when the joint starts to experience loading; and the fixation loosens after the loading is substantially reduced—indicative of relaxation of the joint.

Knee Brace Fixation

During much of the time that the person is wearing the brace, the knee is not bearing the body weight, thus it is not necessary to have the straps of the brace tight during those times. This helps to avoid the discomfort of a load bearing brace. While a person is seated for example there is no need to have the brace fastened uncomfortably tightly. Also while the person is bearing the weight on the fellow leg, there is similarly no need to have the brace uncomfortably tight.

The tightness of the brace is increased as a precursor to application of counter tension. As the foot strikes the floor, a mechanism is activated that increases the tension of both the lower and upper leg collars. The inflation of the bladders is substantially completed before the maximum counter tension is applied to the knee.

The fixation bladder is in fluid communication and fills as a single entity. It is shaped to allow for multiple protuberances to promote better fixation. The protuberances are barb shaped to promote even better fixation in the direction needed, i.e. to provide a very high frictional force that prevents the bottom collar from sliding down and prevents the upper collar from sliding up. The material is chosen for comfort, for high coefficient of friction, for durability and for low compliance. A composite is a good choice including a nylon screen for compliance and silicone for durability, compatibility, low permeability and good friction.

The fluid that fills the fixation bladders has low viscosity so it fills the bladders quickly. It is a liquid so that it is effectively incompressible so that the fixation force is transferred effectively to the interface with the skin.

After load is removed from the foot, the fixation bladder pressure is automatically reduced. While the brace is not tight—there is ample opportunity for good circulation and cooling for comfort.

Many alternatives are possible for the automatic fixation. The fixation apparatus must be deployable and coupled to the load bearing of the joint. The bladder can be multiple chambers or a single. The protuberance can be single or multiple; there may be rings, sawtooth, ridges; they may be circumferential, partial or spot anchors. Many more possibilities exist. The fluid to fill the bladders may be hydraulic or pneumatic. The fixation bladder may consist of separate chambers that are alternately used so that there is an extra relaxation period for the fixation anchor sites. The shape of the pressurized bladder may be designed to facilitate fixation. The bladder shape may be designed to facilitate closure and attachment of the brace.

In fact the automatic fixation can be other than bladders. It can be mechanical; for example—latches that are triggered by load bearing on the leg. It could even be electromechanical—for example a solenoid latch that is triggered by sensing of load bearing on the leg.

In another alternative design, the fixation is automatically held tightly to the leg whenever load bearing is detected and for a period of at least 1 second after the load bearing ceases. In this way, the brace remains tightly secured to the leg during ambulation, but begins to loosen to a more comfortable level during non-load bearing—such as sitting, or standing with weight borne by the fellow leg.

Counter Force

In a preferred embodiment, counter tension is applied to the joint when it is needed and is removed during other times for comfort of the person and for effectiveness. The person with an arthritic knee is not in constant pain while walking. The pain is worst when the knee is forced to bend while bearing the body weight. The weight squeezes out the synovial fluid and sets up the conditions for excruciating pain. When a minute gap is imposed on the joint, the lubrication returns and the pain subsides. This is the case for example when the person uses a cane to divert some of the weight around the knee. This is also the case with a tight unloader brace, though the fixation of an unloader brace is static. With every step, the force of the body weight exerts force to counteract the unloading of the brace. With each step there can be a little slipping. Every little bit of slippage makes the brace less effective; and this can not be counteracted except by a manual readjustment of the brace. In contrast, the brace of the present invention applies counter force to the joint during load bearing and then removes it. Any slippage that occurs during the course of one step is reversed at the end of the step when the brace is driven back by the counter tension mechanism to the start position.

The automatic counter tension mechanism uses the body weight itself to transfer some of the body weight load through the brace external to the body rather than allowing the damaged knee to bear the full weight. The objective is to remove enough load to allow a minute gap between the femur and tibia for a rheological synovial fluid load bearing layer—enough to avoid erosion and pain.

In one embodiment, the energy for the counter tension is harvested from the compression of a collapsible hydraulic container positioned under the foot of the arthritic knee leg. Fluid is displaced from the container. The fluid travels up hydraulic lines (low compliance flexible tubes: braid reinforced polymeric tubes) to automatic fixation bladders and to the counter tension mechanism. The fixation bladders fill quickly and the counter tension mechanism is more gradual. As more and more body weight is placed on the foot (and the underfoot hydraulic container), more and more tension is applied to the knee.

As the maximum body weight is applied, the maximum counter tension is applied to the knee. This maximum force is isometric; i.e. maximum travel of the mechanism is achieved and further travel is prevented by mechanical stops.

In an alternative version, the maximum is isotonic rather than isometric. In this case the mechanism does not reach a stop—the maximum counter tension is thus related to the maximum body load.

The timing between activation of the automatic fixation and the automatic counter tension is important. The brace must be well fixed to the upper and lower leg before the cessation of counter tension. The delay is designed into the hydraulics. A small compliance is built into the line that feeds the counter tension mechanism. This compliance chamber fills almost coincidentally with the fixation bladder. When the compliance chamber fills to its nearly rigid maximum, the fluid pressure in the cylinders drive the pistons forward which apply counter tension to the knee. This fluid resistance/compliance forms a calculable delay analogous to the manner in which electrical resistance and capacitance form an RC time constant.

In an alternative embodiment, the fixation and counter tension mechanisms are connected in series. The hydraulic fluid fills the fixation bladders first (tightly anchoring the brace), and then begins to fill the counter tension activation cylinder driving the pistons forward.

Many variations are possible. Rather than a piston cylinder drive, there may be single or multiple hydraulic chambers, cylindrical, oval or other shape. Rather than hydraulic, the drive may be mechanical (as for example rack and pinion), electro-mechanical or other equivalent.

The direction of the accommodating force can be in a different direction than the axial counter tension load. It could be in the lateral-medial direction or anterior-posterior direction to transfer load away from the arthritic condyle to a healthier portion of the joint.

Alternatively, the separation in the joint can be achieved by application of nearly external pressure circumferentially around the joint. This lengthens the region effectively by a reverse barreling effect.

In the case of the foot/ankle brace, the counter tension is applied by deflating the insole. Once the leg is affixed tightly to the brace/boot, the deflation of the in-sole reduces the compression on the ankle and the bottom of the foot. In an alternative embodiment, force is applied to the leg in an upward direction from the bottom of the brace/boot. This counter tension reduces load on the ankle and foot. The deflation of the in-sole achieves a similar result.

Sources of Counter Tension

In the embodiment of FIG. 9 the source of the counter tension is the body weight collapsing a liquid filled bellows underfoot. When that foot hits the floor, liquid is driven out of the bellow as the height and the volume of the bellows are reduced. The liquid travels up hydraulic lines to the automatic fixation anchor and to the counter tension cylinder. The liquid drives the piston up pushing the hinge up. This transfers through the brace, the skin, fascia, muscle and other tissue to ultimately drive the femur bearing surface slightly away from the tibia bearing surface.

Clearly this same result can be accomplished through many other embodiments. For example rather than a hydraulic drive, the mechanism could use a rigid to transfer the body weight when applied to the foot to mechanically pull the upper leg minutely apart from the lower leg.

Alternatively, as shown in FIGS. 8 and 9, a flexible cable can be used to transfer that force to pull the joint a bit apart.

In other embodiments, the foot actuator could be entirely eliminated. In one example, the energy to provide counter tension is derived from musculoskeletal energy during angulations of the leg.

In yet other embodiments the source of energy for the counter tension is from a stored energy source. This could be for example a battery or capacitor or other electrical energy storage device which would be used to power one or more motors or solenoids to apply motion to the brace; or the energy source could be the weight of the body, the energy from the angulation/articulation of the body, a battery, a capacitor, a spring, a flywheel or equivalent energy source.

In still other embodiments mechanically stored energy would be used for the automatic counter force. The energy could be stored in a pressurized ballast in which there could be a pressurized two phase fluid or a gas pressurized over a liquid. The mechanical energy could be stored in a spring or even a flywheel.

For such systems using external energy sources, it would be desirable to employ partial energy recovery—so that some of the energy expended to drive the joint apart is recovered as it passively returns back to the relaxed state.

Indicator

In other embodiments of the apparel, the accommodation is simply alerting the wearer to the weight bearing of the affected area—rather than applying counter force. The alert can be auditory, visual, tactile or other equivalent. Examples include buzzer, LED state and bell. There are many instances in which an indicator is preferred—making the system open loop rather than closed. The apparel apparatus would sense a heightened level of activity of the wearer, and the processor would determine that the apparel should be tightened for better efficacy. A buzzer could be activated alerting the user who could then decide to depress and hold the button that activates the inflation of the fixation bladders, and then release the button when the desired tightness is achieved.

Joint Load Bearing Sensing

In one embodiment, the joint load bearing sensing is accomplished with an underfoot hydraulic bellows. The mechanism is a liquid filled titanium welded bellows attached near the heel of the foot wear of the person. The bellows has an exit that is attached to low compliance hydraulic line that feeds into the automatic fixation and counter tension mechanisms.

The bellow can alternatively be constructed differently with other materials or constructions. It can have multiple exits. It could be polymeric or metallic. Rather than a convoluted bellows it could be more amorphous—as long as the walls exhibit low compliance. In fact, the mechanism could be piston within a cylinder (or other effective shape). It may be located under foot or alongside as long as it is situated to bear at least a portion of the body weight.

When coupled with an energy source other than the body weight, the foot actuator could take other forms. The actuator could be just a sensor to detect foot fall. A heel mounted load cell would work. Alternatively an accelerometer, microphone or equivalent could detect footfalls and even be mounted on the brace rather than under foot.

In yet another embodiment, an underfoot mounted piezo device could detect footfalls and even provide the power for the counter tension.

In still other embodiments, the sensor detects the need for counter tension by movement of the joint. For example, in upper body joints, the joint may be relatively comfortable while stationary. Any movement of the joint may elicit pain; thus any movement would be detected and used to activate the counter tension mechanism of the brace. For example, when the position or angle of the humerus is changed relative to the radius—it is indicative that the elbow joint is being used and that counter tension should be applied. One way this could be accomplished is with a cam hinge. For any movement of the joint, counter tension is applied—the hinge rides on the high portion of the cam during such times. At rest, the cam rotates so that the joint is on a low point of the cam—counter tension is removed. The cam is pulled to this low point (relaxed) position by a spring and dampener—so that counter tension is applied to the joint any time there is motion—and counter tension is removed when the joint is at rest.

In another embodiment standing and walking are detected with data from an accelerometer as interpreted by the processor. Sensing of standing requires accelerometer confirmation of verticality. Sensing of walking requires detection of a predictable regular swing of the detected angle of the accelerometer.

Sensing of the need for accommodation can be accomplished with many different sensors. Sensing any appropriate variable or parameter is acceptable. Deviation from a resting value of the variable or parameter should indicate a need for brace accommodation. It can have different values for example that indicate sitting, standing, walking, running, jumping etc. It can require processing, such as digital filtering. There should be a range indicative of rest, and non-rest. Even more desirable is an indicator that gives gradation of need for accommodation; this would allow for proportional control. In a proportionally controlled brace, the magnitude of the accommodation would vary with the magnitude of the sensed parameter. For example, running mandates more accommodation (such as counter force and fixation pressure) than does walking.

Knee Brace Hinge

The hinge is a simple pivot, though any coupling known in the art is acceptable. There may be a complex hinge, a simple arc or compound arc. There may be a cam and follower.

The hinge may by symmetric or asymmetric. There may be a single hinge on one side of the leg or preferably both sides.

The foot/ankle brace in particular may function best with a locked hinge. For comfort, it may be desirable to have the hinge unlocked at times, for example in the absence of load bearing. In one embodiment, the hinge is free to move except when loading of the body part is detected, whereupon the hinge is restricted or locked by the brace.

Knee Brace Controls

In the preferred embodiment the control of the brace is accomplished automatically via hydraulic sensing/activation mechanisms. An underfoot hydraulic bellows container senses the load bearing—as liquid is pushed by the body weight out of the bellows. Activation is accomplished as the liquid that exits the bellows enters the deployable fixation chambers and then the counter tension activation cylinders.

There are other acceptable alternatives. Other acceptable sensors are other force, pressure or acceleration sensors. The sensor could be located where it bears body weight, but it is also acceptable to be located elsewhere as long as it still senses footfalls.

The activation control in the preferred embodiment is an automatic hydraulic mechanism, but it may be other control mechanism, such as analog electrical, digital electrical or other equivalent control. Use of microprocessor control for example would enable complex timing relating weight bearing, fixation deployment and counter tension activation.

Discrimination of standing, walking, jogging, running, jumping and other physical activities can be interpreted from the data. The brace can accommodate for each of these sensed activities accordingly. For example, the fixation pressure will be higher for jumping and running than it is for standing and walking.

Applications

The brace is intended to promote patient compliance. It is comfortable enough while the wearer is at rest that the wearer does not remove it prematurely. The brace is meant to accommodate to the demands of the wearer. While at rest, the brace is comfortable; during walking, the brace deploys the fixation and/or counter force elements.

Embodiments have been described for exemplary markets. Accommodating braces that divert some load around a foot ulcer or an arthritic knee joint have been described.

The brace may be applied to other joints. It may be used in a similar manner for a sacroiliac, hip joint, vertebral joints, etc. It could even be used for a finger, wrist, elbow, neck or shoulder joint.

Other embodiments include athletic footwear: sneakers, ski boots or snowboard boots that tighten when activity is sensed and loosen when the athlete is at rest. In athletic footwear the improved fixation is intended to enhance performance. In a snowboard boot for example, increasing tightness during aggressive riding is intended to provide more rapid weight transfer from the body to the turning edges of the board. Enhanced activity is planned for other sports wear as well.

Casual footwear applications are similar, e.g. shoes that automatically fasten when the foot is inserted. These might be particularly useful for toddler shoes or for adult loafers. This adds convenience for the casual wearer and the athlete; it adds functionality in children's footwear, as the children may not yet have the capacity to properly affix footwear.

Yet other applications include apparel for other body parts; for example a belt that senses motion and enhances back support. During a swing, it allows a golfer to hit a ball more forcefully. During daily activity, it provides support when lifting and helps to reduce shock on the spine. Thus apparel of the present invention may be designed for knee, ankle, plantar surface of the foot, hip, vertebra, elbow, finger back, neck or other.

Additional Features

In addition to the features described, the brace can provide other benefits; in particular reducing edema and improving circulation. Because the brace includes bladders, valves, a pump and a controller, the bladders can be filled in a manner that accomplishes unloading of a body part when needed. That same hardware can also be used in a sequentially activated manner that facilitates the reduction of edema, or the improvement of venous blood egression flow and arterial blood ingression. Low pressure sequential pressurization of the bladders (in the retrograde direction to push fluid back towards venous drainage into the heart) then venting can be used to gently and gradually reduce edema that is especially common in those with foot ulcers. Pressure would generally be less than 20 mm Hg. Occasionally, higher pressure sequential pressurization then venting can be used in the antegrade direction can be used to assist arterial blood flow towards the body part. This may be on the order of 100 mm Hg pressure so that it can assist in the "peristaltic" pumping of arteries.

Modifications

Thus, specific embodiments and applications have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A brace apparatus for at least partial unloading of an ankle joint of a leg of a person, wherein the ankle joint bears a compressive load during use, wherein the compressive load is substantially smaller when the ankle joint is at rest than when the ankle joint is active, comprising
   a collar positioned about the leg between an ankle and a knee of the person;
   an electronic sensor;
   a fixation bladder within the collar, responsive to input from the sensor, and configured to at least semi-automatically increase a fixation pressure of the collar about the leg;
   a brace structure configured to support a compressive load, and having (a) a proximal end attached to the collar, and (b) a distal end that is positioned to contact the ground beneath the ankle; and
   an unloading insole attached to the brace structure configured at least semi-automatically to transfer a portion of the compressive load from the joint to the brace structure when the joint bears the load.

2. The brace apparatus of claim 1 wherein the unloading insole is configured to transfer the portion of the compressive load from the joint to the brace structure after the increase of the fixation pressure of the collar about the leg.

3. The brace apparatus of claim 2, wherein the unloading insole is configured to transfer the portion of the compressive load from the joint to the brace structure after the increase of the fixation pressure of the collar about the leg in a period of time that is on the order of one minute.

4. The brace apparatus of claim 1, wherein the unloading insole is chosen from a list including: a viscoelastic insole, a passive pneumatic bladder, a bladder in fluid communication with a pump and vent switch.

5. The brace apparatus of claim 1, wherein the unloading insole is configured to reduce a pressure against a plantar surface of a foot of the leg when the joint bears the load.

6. The brace apparatus of claim 1 further comprising an automatic closure mechanism having an open state and a closed state, wherein the automatic closure mechanism is configured to provide an opening large enough to readily insert a foot into the brace apparatus when in the open state, wherein the mechanism is configured to be closed around the leg when in the closed state and wherein the automatic closure mechanism is triggered by the electronic sensor.

7. The brace apparatus of claim 1, wherein the fixation bladder is configured to automatically increase the fixation pressure when the joint bears the compressive load, and to automatically reduce the fixation pressure when the compressive load is removed.

* * * * *